(12) United States Patent
Massad

(10) Patent No.: US 7,273,371 B2
(45) Date of Patent: Sep. 25, 2007

(54) DENTAL TRAY FOR OBTAINING DENTAL IMPRESSION OF EDENTULOUS PATIENT

(75) Inventor: Joseph James Massad, Tulsa, OK (US)

(73) Assignee: Global Dental Impression Tray, Inc., Tulsa, OK (US)

( * ) Notice: Subject to any disclaimer, the term of this patent is extended or adjusted under 35 U.S.C. 154(b) by 0 days.

(21) Appl. No.: 11/393,560

(22) Filed: Mar. 30, 2006

(65) Prior Publication Data

US 2006/0223025 A1    Oct. 5, 2006

Related U.S. Application Data

(60) Provisional application No. 60/667,632, filed on Apr. 2, 2005.

(51) Int. Cl.
*A61C 9/00* (2006.01)

(52) U.S. Cl. ....................................... 433/37

(58) Field of Classification Search .................. 433/37, 433/38, 41, 45, 47
See application file for complete search history.

(56) References Cited

U.S. PATENT DOCUMENTS

| | | | |
|---|---|---|---|
| 3,473,225 A * | 10/1969 | Deuschle et al. ............. | 433/48 |
| 5,026,278 A | 6/1991 | Oxman et al. | |
| 5,076,785 A * | 12/1991 | Tsai ............................ | 433/46 |
| 5,316,474 A | 5/1994 | Robertson | |
| 5,478,235 A | 12/1995 | Schuldt et al. | |
| D372,088 S | 7/1996 | Frush | |
| D372,096 S | 7/1996 | Frush | |
| 5,772,432 A | 6/1998 | Jordan et al. | |
| 6,079,977 A | 6/2000 | Persichetti | |
| 6,213,768 B1 * | 4/2001 | Wright ........................ | 433/37 |
| 6,428,315 B1 | 8/2002 | Prestipino et al. | |
| 6,457,973 B1 | 10/2002 | Fetz et al. | |
| 6,641,393 B2 | 11/2003 | Trichas | |
| 6,749,428 B2 | 6/2004 | DiMarino et al. | |

* cited by examiner

*Primary Examiner*—Melba Bumgarner
(74) *Attorney, Agent, or Firm*—Steven R. Tollette; Mark G. Kachigian

(57) ABSTRACT

A dental tray having a body, at least two finger rest beams and a handle. The body has a predetermined shape and a plurality of body openings. The predetermined shape of the body accommodates the anatomical shape of the patient's mouth and receives the entire jaw and gingiva areas. The plurality of body openings positioned in the body to allow the impression materials to vent through the body openings to obtain the impression and to retain the impression materials onto the body. The handle is received on the body and has a predetermined configuration to facilitate ease of use and elimination of lip pressure. Each finger rest beams are received longitudinally on the bottom of the body. The combination of the handle and each finger rest beams are ergonomically designed to allow optimal stabilization pressure be exerted by the operator to the dental tray and impression material.

12 Claims, 12 Drawing Sheets

DENTAL TRAY FOR OBTAINING DENTAL IMPRESSION OF EDENTULOUS PATIENT

CROSS REFERENCE TO RELATED APPLICATION AND BENEFIT OF EARLIER FILING DATE

This application is based upon U.S. Provisional Patent No. 60/667,632 filed on Apr. 2, 2005 entitled "Dental Tray For Obtaining Dental Impression Of Edentulous Patient". This U.S. Letters Patent Application is claiming the benefit of the Apr. 2, 2005 filing date under 35 U.S.C. Section 119(e).

BACKGROUND OF THE INVENTION

1. Field of the Invention

This invention relates to a new dental impression tray, used in combination with moldable material, for obtaining an accurate impression of the jaw and gingiva areas of the mouth of an edentulous patient.

2. Prior Art

In dentistry, an impression is often used to create an imprint likeness of an edentulous patient's jaw and gingiva areas in preparation for restoration of dental structures such as complete or partial dentures. The ability of the dental technician or dentist, hereinafter referred to as "operator", to obtain a satisfactory impression is influenced by the dental impression tray, hereinafter referred to as either "dental impression tray" or "dental tray", used in combination with moldable material, hereinafter referred to as "impression material", to obtain the impression.

The accuracy of the impression, to a large extent, will depend upon how well the dental tray is received in the patient's mouth. In order to gain a more accurate impression, numerous types of dental trays have been developed. Some dental trays are designed for numerous applications and are called standard dental trays. Some dental trays are specifically designed for a single purpose such as a dental tray designed for only one side of a patient's mouth. Some dental trays are designed for use with a patient that still has at least some of their teeth as disclosed in U.S. Pat. No. 6,457,973 B1, issued on Oct. 1, 2002 to Fetz et al. Some dental trays are adjustable to allow one dental tray to fit a large number of patients as disclosed in U.S. Pat. No. 6,428,315 B1, issued on Aug. 6, 2002 to Prestipino et al. Some dental trays are designed to allow impression material to be placed in the patient's mouth through the dental tray after inserting the tray in the patient's mouth as disclosed in U.S. Pat. No. 6,641,393 B2, issued on Nov. 4, 2003 to Trichas. Some dental trays, called enhanced trays, are larger devices that that help lift the patient's tongue up and away from the jaw and gingiva areas to assist with obtaining an impression. It is also very common for the dental trays in the prior art to require the use of adhesive to help retain the impression material onto the dental tray during the impression procedure. The adhesive is odorous and distasteful, making the use of adhesives unpleasant for the patient.

While each of the different trays in the prior art do address certain problems with obtaining an accurate impression, they also create new problems or do not work well with today's wide range of impression materials. One problem is that prior art causes excessive impression material to be expelled backward into the throat of the patient causing discomfort and sometimes gagging. Another problem is that the prior art are not built to match the anatomy of an edentulous patient's jaw and gingiva areas. This can lead to the dental tray deforming the patient's jaw and gingiva areas, thus preventing an accurate impression. This also leads to having to use excessive impression material to obtain a reasonable impression, which contributes to a patient's discomfort and gagging. Yet another problem is that the prior art does not work well with the entire range of impression materials that are now available from extralight to very heavy in density due to openings in the dental trays having either too small of openings or too large of openings. Where the dental tray has small openings, the dental tray does not distribute the medium to very heavy density impression materials well. Where the dental tray has large openings, the dental tray does not retain the extralight to medium density impression materials well. This causes the operator to use impression materials that work with the dental tray when other types of impression materials or a combination of different types of impression materials would provide better results. Yet another problem is that the prior art does not provide a means for uniformly distributing pressure to the dental tray to seat the dental tray and impression material in the patent's mouth. When inserting the dental tray and impression material in the patient's mouth, the operator must push on the tray to seat it around the jaw and gingiva areas. Since the prior art does not provide a way to distribute this pressure uniformly to the dental tray, often the dental tray will improperly seat deeper at the point where the pressure is applied and create an inaccurate impression. Yet another problem is that the prior art does not provide a way to allow the operator to keep their hand, wrist and arm in an ergonomically correct position while placing the dental tray and impression material in the patient's mouth and while placing pressure on the dental tray to seat the dental tray and impression material. At best, this can lead to the operator's fatigue, discomfort and loss of productivity; and, at worse, can lead to the operator becoming injured by having to repetitively place their hand, wrist and arm in awkward positions.

Therefore, there is a need in the art for a new and improved dental tray that provides an accurate impression of an edentulous patient's jaw and gingiva areas by more closely matching the anatomy of the edentulous patient's mouth so that the patient's jaw and gingiva areas are not deformed or influenced by the dental tray and the impression material is retained by the dental tray during the impression procedure without the use of adhesives; by accommodating the use of the entire range of impression materials that are now available so that the best impression material or the best combination of impression materials can be used to obtain the impression; by providing a means to uniformly transfer pressure to the dental tray so that the impression material is correctly seated in the patient's mouth to obtain an accurate impression with less discomfort to the patient; and by providing a dental tray that allows the operator to maintain their hand, wrist and arm in an ergonomically correct and comfortable position while placing the dental tray and impression material into the patient's mouth and while seating the dental tray and impression material in the patient's mouth during the process of obtaining the dental impression of the edentulous patient.

SUMMARY OF THE INVENTION

It is an object of this invention to provide a new dental tray for obtaining an accurate impression of the jaw and gingiva areas of the mouth of an edentulous patient where the dental tray has a predetermined shape that accommodates the anatomical shape of the edentulous patient's jaw and gingiva areas so that the patient's jaw and gingiva areas are not deformed or influenced by the dental tray and the impression material is retained by the dental tray, without the need for adhesives on the dental tray to help retain the impression material, during the impression procedure.

Another object of this invention is to provide a new dental tray for obtaining an impression of the jaw and gingiva areas of the mouth of an edentulous patient that can be used with the entire range of impression materials from extralight to very heavy in density and can be used with a combination of different density impression materials to obtain an accurate impression.

Yet another object of this invention is to provide a new dental tray for obtaining an impression of the jaw and gingiva areas of the mouth of an edentulous patient that provides a means to uniformly transfer pressure applied by the operator to the dental tray so that the combination of the dental tray and the impression material is correctly seated in the patient's mouth to obtain an accurate impression with less discomfort to the patient, while allowing the operator to maintain their hand, wrist and arm in an ergonomically correct and comfortable position during the impression procedure.

To meet the objectives of the invention, the new dental tray comprises a body, at least two finger rest beams and a handle. The body having a body front end and a body rear end. The handle is attached to the body front end of the body so that the handle can be used to insert and remove the dental tray from the patient's mouth when the impression material is applied to the body of the dental tray and where the handle is narrow enough to allow the operator to negotiate placement of the dental tray without trapping open their fingers. Each of the finger rest beams are received longitudinally along the bottom side of the body and are specifically located on the body such that any pressure placed upon each of the finger rest beams will transfer along the length of each of the finger rest beams and into the body uniformly. The longitudinal length of each of the finger rest beams allow for different sized fingers of the operator to be accommodated anywhere along each of the finger rest beams. Each of the finger rest beams are connected to the handle, where the handle is also attached to the body, such that the combination of the body, handle and each of the finger rest beams form the dental tray.

The body comprises an upstanding outer wall portion, a channel portion and a central support portion having a predetermined shape that accommodates the anatomical shape of the edentulous patient's jaw and gingiva areas and a plurality of body openings. The shape of the body, being substantially close to the anatomy of the edentulous patient's jaw and gingiva areas, is designed to allow the body to retain a wide range of impression materials without directing the flow of the impression materials and without influencing or deforming the jaw and gingiva areas. The plurality of body openings further comprises a plurality of dumbbell shaped body openings and a plurality of circular shaped body openings. The plurality of dumbbell shaped body openings having a variety of sizes and orientations and the plurality of circular shaped body openings having a predetermined size. The dumbbell shaped body openings and the circular shaped body openings are positioned in the body at predetermined locations. This combination of openings cooperate to allow the impression material to vent through these openings with the least resistance to obtain the impression of the jaw and gingiva areas, while acting to retain the impression material until it is cured to prevent distortion of the impression material. In another embodiment of the invention, the body further comprises a thickened edge and a plurality of edge notches. The thickened edge being substantially circular in shape with a predetermined diameter and being received along the outer edge of the upstanding outer wall portion, the channel portion and the central support portion of the body to capture the anatomical features of the patient's mouth while the plurality of edge channels provide additional surface area to retain the layer of impression material on the thickened edge until it is cured to prevent distortion of the impression material. These features allow the body to successfully use a wide range of impression materials that vary from extralight to very heavy in density.

The new dental tray described in this invention is for the edentulous patient without teeth or without substantial crowns. The dental tray is designed to have a predetermined shape that accommodates the anatomical shape of the edentulous patient's jaw and gingiva areas to allow the dental tray to retain the impression material without inhibiting or directing the flow of the impression and without influencing or deforming the jaw and gingiva areas while the jaw and gingiva areas are being imprinted by the impression material. The dental tray will act as a carrier to hold any one of the entire range of impression materials from extralight to very heavy in density or any combination of different density impression materials distributed in the dental profession. The combination of the plurality of dumbbell shaped body openings and plurality of circular shaped body openings cooperate to allow the impression materials to vent through these openings with the least resistance to obtain the impression of the jaw and gingiva areas, while acting to retain the impression material until it is cured to prevent distortion of the impression materials. The rounded, thickened edge of the body allows the impression material to capture anatomical features of the edentulous patient and the edge channels help retain this layer of impression material on the thickened edge and body until it cures. The development of special finger rests allows uniform seating of the trays in the patient's mouth while allowing the operator to keep their hand, wrist and arm in an ergonomically correct position. The dental trays are to be made in various sizes to accommodate the highest percentage of the edentulous population. The dental tray can be made from metal, metal plated with other metal or plastic or moldable plastic. The moldable plastic dental tray wall thickness has been selected to allow localized reshaping by the operator of the predetermined shape of the body by either trimming with a bur or heating with a flame and remolding to obtain a personalized dental tray to better fit the patient's jaw and gingiva areas. The invention is unique because it is shaped to closely match the anatomy of an edentulous patient's mouth; it uses a combination of different shaped holes in the body of the tray; if made from moldable plastic material, the body of the dental tray can be locally reshaped; it has a rounded thickened edge with edge channels to allow the impression material to capture the anatomy of an edentulous patient's mouth without deforming the jaw and gingiva areas; it uses each of the finger rest beams to uniformly seat the dental tray to obtain an accurate impression; and the combination of the handle and each of the finger rest beams cooperate to allow the operator to keep his or her hand, wrist and arm in an ergonomically correct position while inserting, seating and holding the dental tray and impression material during the impression process; and uses a minimum amount of impression material to obtain the impression without restricting the type of impression materials that can be used with the dental tray.

BRIEF DESCRIPTION OF THE DRAWINGS

These and other features, aspects, and advantages of the present invention will become better understood with respect to the following description and accompanying drawings where.

DETAIL DESCRIPTION OF THE INVENTION

Figure 1:
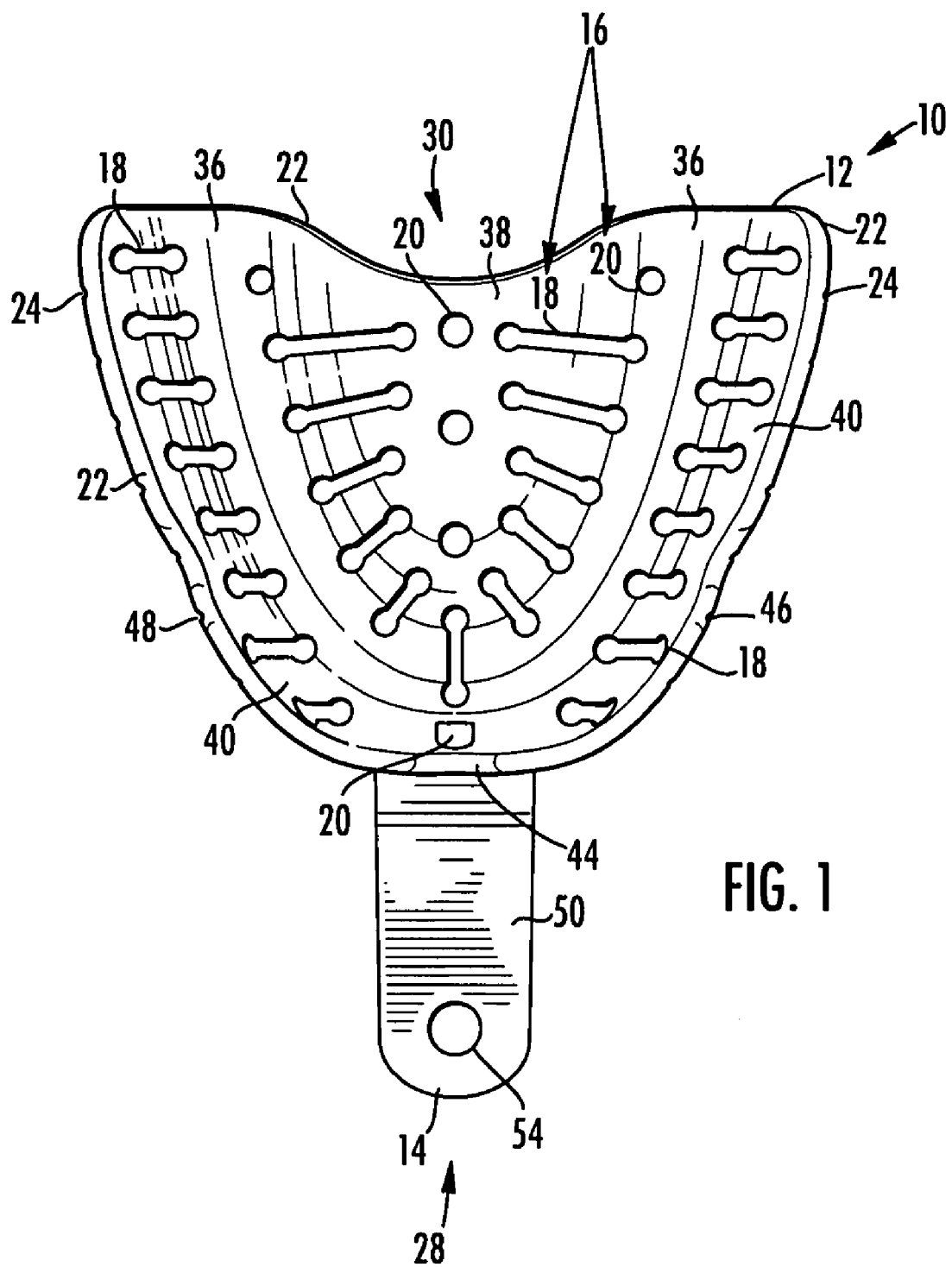
FIG. 1 is a top view of one embodiment of the invention.
Figure 2:
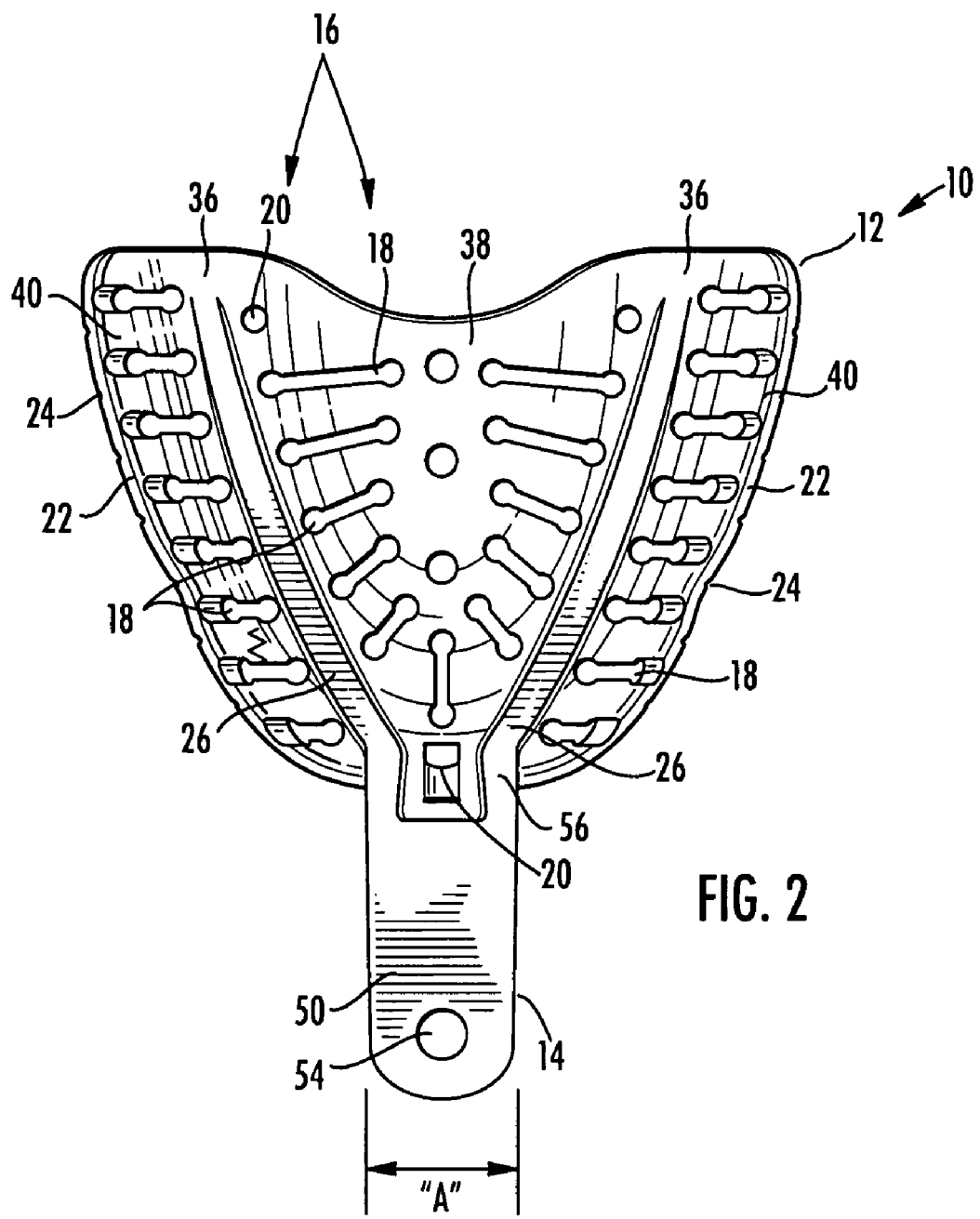
FIG. 2 is a bottom view of the embodiment of the invention shown in FIG. 1.

Referring to the figures of the drawings, wherein like numerals of reference designate like elements throughout the several views, particularly to FIG. 1, there is shown a top view of a dental impression tray 10 to be used in combination with an impression material or a combination of impression materials for obtaining an impression of the jaw and gingiva areas of the mouth of an edentulous patient, where the impression material is not shown. As shown in FIGS. 1 through 12, the dental impression tray 10 comprises a body 12, at least two finger rest beams 26, and a handle 14. As shown in FIG. 1, the body 12 has a body front end 28, a body rear end 30, a predetermined shape of the body 12, and a plurality of body openings 16. FIGS. 1 through 6 show one embodiment of the invention and FIGS. 7 through 12 show a second embodiment of the invention. The predetermined shape of the body 12 accommodates the anatomical shape of the edentulous patient's mouth and is dimensioned and configured to be placed around the entire jaw and gingiva areas while retaining the impression material.

The dental impression tray 10 can be made from a variety of materials such as metal; metal plated with other metal such as steel plated with chrome or steel plated with stainless steel; metal coated with plastic material such as steel plated with a polymer or resin material; or heat moldable plastic material such as polymer or resin. In the preferred embodiment of the invention, the dental impression tray 10 is made from a thermoplastic polymer material, where the preferred thermoplastic polymer material is polystyrene.

It is desirable to have the body 12 of the dental impression tray 10 be capable of being locally reshaped by the operator to allow the body 12 to better fit the patient's mouth. The body 12 should fit comfortably over the edentulous ridge with a two-to-four millimeter clearance. Being able to reshape the body 12 to obtain this clearance is extremely important to obtaining an accurate impression. In the prior art, the body of these dental trays are not reshapeable because they are made from metal or are made from plastic material that cannot be reheated to allow them to be remolded or are made from plastic with a body thickness that is either too thin or too thick to be heated and remolded. For the heat moldable plastic material, such as polystyrene material, it has been determined that a body 12 having a thickness between 0.072 inches and 0.094 inches would allow the body 12 to be reshaped by: (1) heating the part of the body 12 that needs to be reshaped with an open flame, under controlled conditions; (2) remolding the heated part of the body 12 using the operator's fingers while the body 12 is still warm; and (3) setting the new shape of the body 12 by placing the body 12 in a dish of cool water until the body 12 is set again. It was determined that a body 12 thickness of less than 0.072 inches had difficulty withstanding the manual remolding as the body 12 tends to want to fold over when heated or not hold the new remolded position; and a body 12 thickness of more than 0.094 inches could not be manually heated uniformly enough to allow the body 12 to be properly adjusted with just the operator's fingers. The thickness of the body 12 also affects the operator's ability to reshape the body 12 by trimming the body 12, where an external cutter such as a dental bur accomplishes the trimming. If the body 12 is too thin, then the operator can quickly remove more of the body 12 than they intend to and have to dispose of the dental tray. If the body 12 is too thick, then the operator has to spend a lot of time to take off more material and may fail to remove enough without repeated attempts. Having a thickness of the body 12 being between 0.072 inches and 0.094 inches in heat moldable plastic material, such as polystyrene material, was a reasonable thickness given the ease at which a dental bur could remove the heat moldable plastic material, such as polystyrene material, to reshape the body 12.

A body 12 made from moldable plastic material, such as polystyrene, and having a thickness between 0.072 inches and 0.094 inches will allow localized reshaping of the body 12 (1) by heating and remolding the body 12, where heating is accomplished with an external heating source such as an open flame, or (2) trimming of the body 12, where trimming is accomplished by an external cutter such as a dental bur, such that the reshaping of the body 12 allows the predetermined shape of the body 12 to be modified to specifically accommodate the patient's jaw and gingiva areas which prevents deforming the jaw and gingiva areas of the patient's mouth when the dental impression tray 10 is used in cooperation with impression materials to obtain an impression.

As shown in FIGS. 1, 2, 5, 6, 7, 8, 9, 11, & 12, the body 12 comprises an upstanding outer wall portion 40, a channel portion 36, and a central support portion 38, where the upstanding outer wall portion 40 is connected to the central support portion 38 by the channel portion 36 to form the body 12. The upstanding outer wall portion 40 having a first wall notch 44, a second wall notch 46 and a third wall notch 48 located along the top edge of the upstanding outer wall portion 40, where the first wall notch 44, the second wall notch 46 and the third wall notch 48 accommodate the muscle attachment locations in the patient's jaw areas. The first wall notch 44, the second wall notch 46 and the third wall notch 48 being substantially V-shaped. The first wall notch 44 is located in the upstanding outer wall portion 40 at the center of the body front end 28. The second wall notch 46 and third wall notch 48 are located in the sides of the upstanding outer wall portion 40 approximately ⅓ of distance between the body front end 28 and the body rear end 30 such that the second wall notch 46 and the third wall notch 48 are closer to the body front end 28 than to the body rear end 30. The central support portion 38 has a substantially curved end at the body rear end 20. The substantially curved end in the central support portion 38 shown in FIGS. 1 through 6 are for capturing the functional hard-soft palate throat form of the upper jaw. The substantially curved end in the central support portion 38 shown in FIGS. 7 through 12 accommodate the sublingual gland and fatty tissue, of the lower jaw to allow capturing of the mylohyoid space. As seen in FIGS. 1 through 12, the combination of: (1) the upstanding outer wall portion 40 containing the first wall notch 44, the second wall notch 46 and the third wall notch 48, (2) the channel portion 36 and (3) the central support portion 38 containing the curved end at the body rear end 30, have a predetermined shape and have a plurality of body openings 16. The predetermined shape accommodates the anatomical shape of the edentulous patient's mouth and is dimensioned and configured to be placed around the entire jaw and gingiva areas while retaining the impression materials.

As shown in FIGS. 1 through 12, the upstanding outer wall portion 40, the channel portion 36 and the central support portion 38 contain a plurality of body openings 16. The plurality of body openings 16 comprises a plurality of substantially dumbbell shaped body openings 18 and a plurality of substantially circular shaped body openings 20. The dumbbell shaped body openings 18 having a variety of sizes and orientations depending on where they are located in the dental impression tray 10. The circular shaped body openings 20 having a predetermined size as shown in FIGS. 1 through 6 for one embodiment of the invention and as shown in FIGS. 7 through 12 for another embodiment of the invention. As shown in FIGS. 1 through 12, the dumbbell shaped body openings 18 and the circular shaped body openings 20 are positioned in the upstanding outer wall portion 40, the channel portion 36 and the central support portion 38 at predetermined locations such that the combination of the size, shape and location of the dumbbell shaped body openings 18 and the circular shaped body openings 20 cooperate with the upstanding outer wall portion 40, the channel portion 36 and the central support portion 38 to: (1) allow the impression material or a combination of impression materials to vent through the dumbbell shaped body openings 18 and the circular shaped body openings 20 to obtain the impression of the jaw and gingiva areas of the patient by providing more openings and by providing larger openings than previous prior art in order to make it easier for the impression material to flow to any void spots that may exist around the jaw and gingiva areas, and (2) retain the impression material or a combination of impression materials on the upstanding outer wall portion 40, the channel portion 36 and the central support portion 38 by providing more surface area for the impression material or a combination of impression materials to adhere to without the use of adhesive. In particular, the combination of the dumbbell shaped body openings 18 and the circular shaped body openings 20 are designed to "lock in" the polyvinal siloxane impression material, making the use of an odorous and distasteful tray adhesive unnecessary.

As shown in FIGS. 1 through 12, the upstanding outer wall portion 40, the channel portion 36 and the central support portion 38 has a thickened edge 22 being received along the outer edge of the upstanding outer wall portion 40, the channel portion 36 and the central support portion 38. The thickened edge 22 being substantially circular in shape and having a predetermined diameter such that the diameter of the thickened edge 22 is slightly larger that the thickness of the body 12 to provide more surface area to improve retention of the impression material on this part of the dental impression tray 10 and to reduce the pressure against the jaw and gingiva areas. The thickened edge 22 is designed to capture the full extent of the edentulous ridge and surrounding anatomy without exerting unwanted pressure while retaining the impression material on the body 12. It has been determined that the best results are obtained when the diameter of the thickened edge 22 is between 0.075 inches and 0.142 inches such that the thickened edge 22 cooperates with the body 12 and the impression material or a combination of impression materials to retain a layer of impression material onto the thickened edge 22 in order to capture the impression.

As shown in FIGS. 1 through 12, the thickened edge 22 has a plurality of edge notches 24. The plurality of edge notches 24 are positioned perpendicular to the thickened edge 22 at predetermined locations on the exterior and interior of the thickened edge 22 such that the plurality of edge notches 24 cooperate with the thickened edge 22 and the impression material to retain the impression material on the body 12 by providing additional surface area to retain the layer of impression material on the thickened edge 22.

As shown in FIGS. 2, 3, 4, 5, 8, 9, 10, and 11, the dental impression tray 10 has at least two finger rest beams 26. Each of the finger rest beams 26 are substantially a square shaped ridge received longitudinally on the exterior of the channel portion 36 of the body 12 such that each of the finger rest beams 26 are substantially located underneath the areas of the channel portion 36 that is to be placed around the jaw and gingiva areas of the patient and are specifically located on the channel portion 36 of the body 12 such that any pressure placed upon each of the finger rest beams 26 will transfer along the length of each of the finger rest beams 26 and into the body 12 uniformly. Each of the finger rest beams 26 are connected to the handle 14, where the handle 14 is also received on the channel portion 36, such that the handle 14 and each of the finger rest beams 26 cooperate to provide a mechanism to be used to engage the jaw and gingiva areas with the combination of the dental impression tray 10 and impression material or a combination of impression materials. Each of the finger rest beams 26 are located along the entire length of the bottom of the channel portion 36 in order to accommodate different operator's finger lengths. For example, if an operator has short fingers they can place their fingers on each of the finger rest beams 26 close to the body front end 28 and if an operator has long fingers they can place their fingers on each of the finger rest beams 26 near the body rear end 30. Each of the finger rest beams 26 are designed to distribute the pressure applied by the operator to the each of the finger rest beams 26 uniformly onto the dental impression tray 10 to correctly seat the dental impression tray 10 and the impression materials around the jaw and gingiva areas of the edentulous patient's mouth. Each of the finger rest beams 26 are designed to allow optimal stabilization pressure be transferred from the operator's fingers to the dental impression tray 10 while allowing the operator to maintain the correct ergonomic position of his/her hand, wrist and arm.

Figure 3:
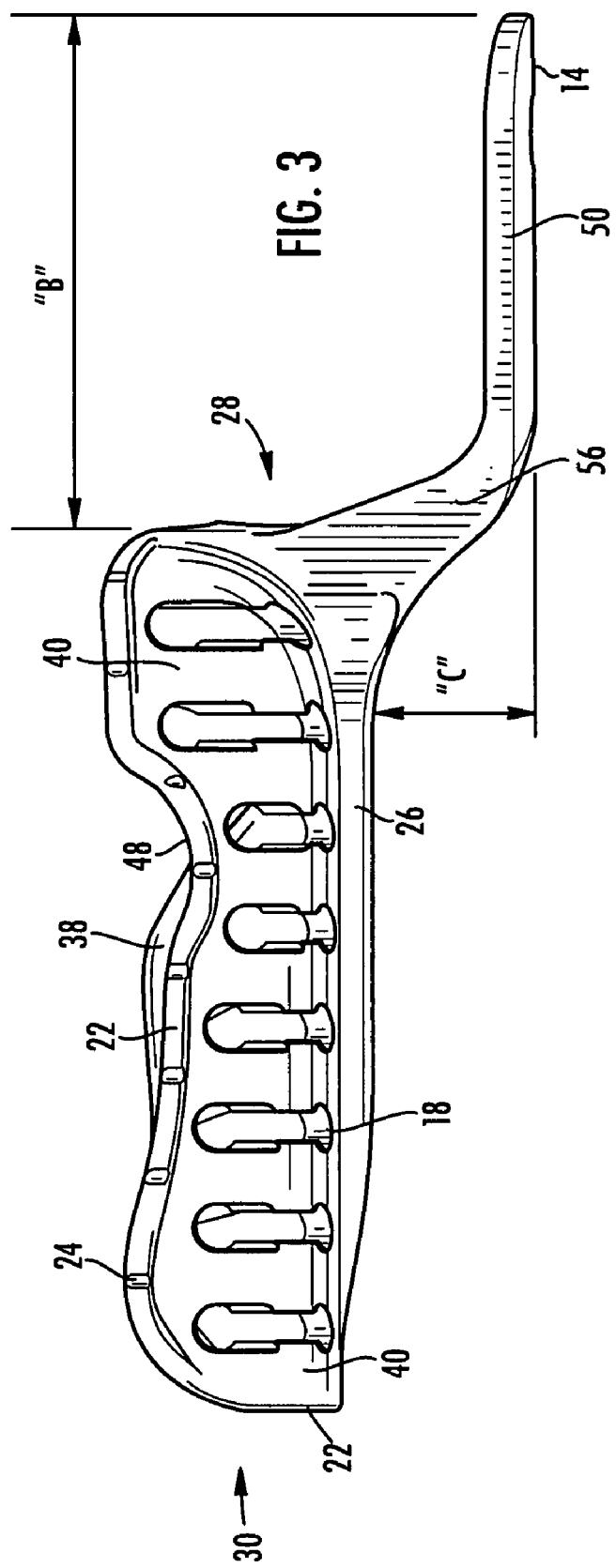
FIG. 3 is a side view of the embodiment of the invention shown in FIG. 1.
Figure 4:
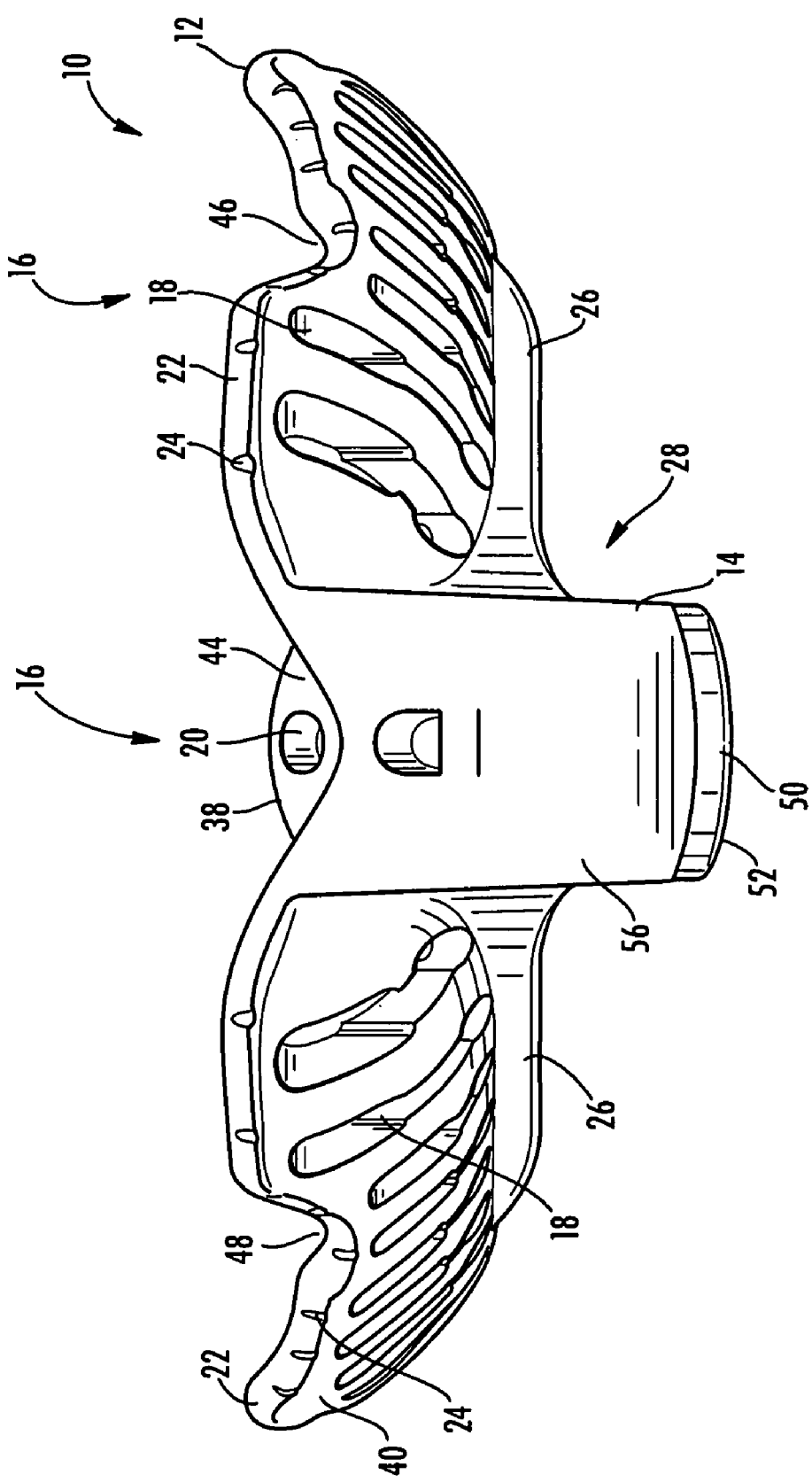
FIG. 4 is a front view of the embodiment of the invention shown in FIG. 1.
Figure 5:
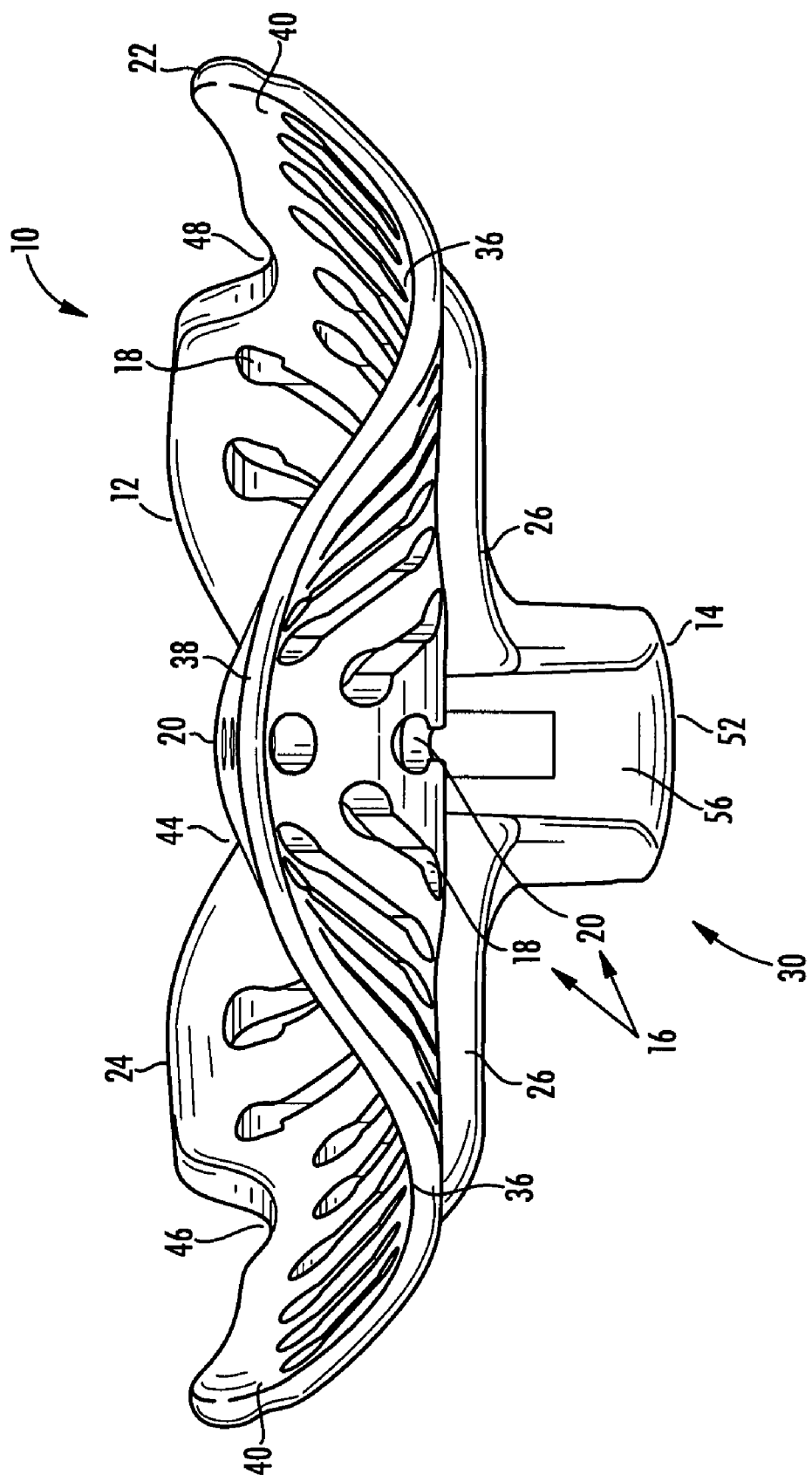
FIG. 5 is a rear view of the embodiment of the invention shown in FIG. 1.
Figure 6:
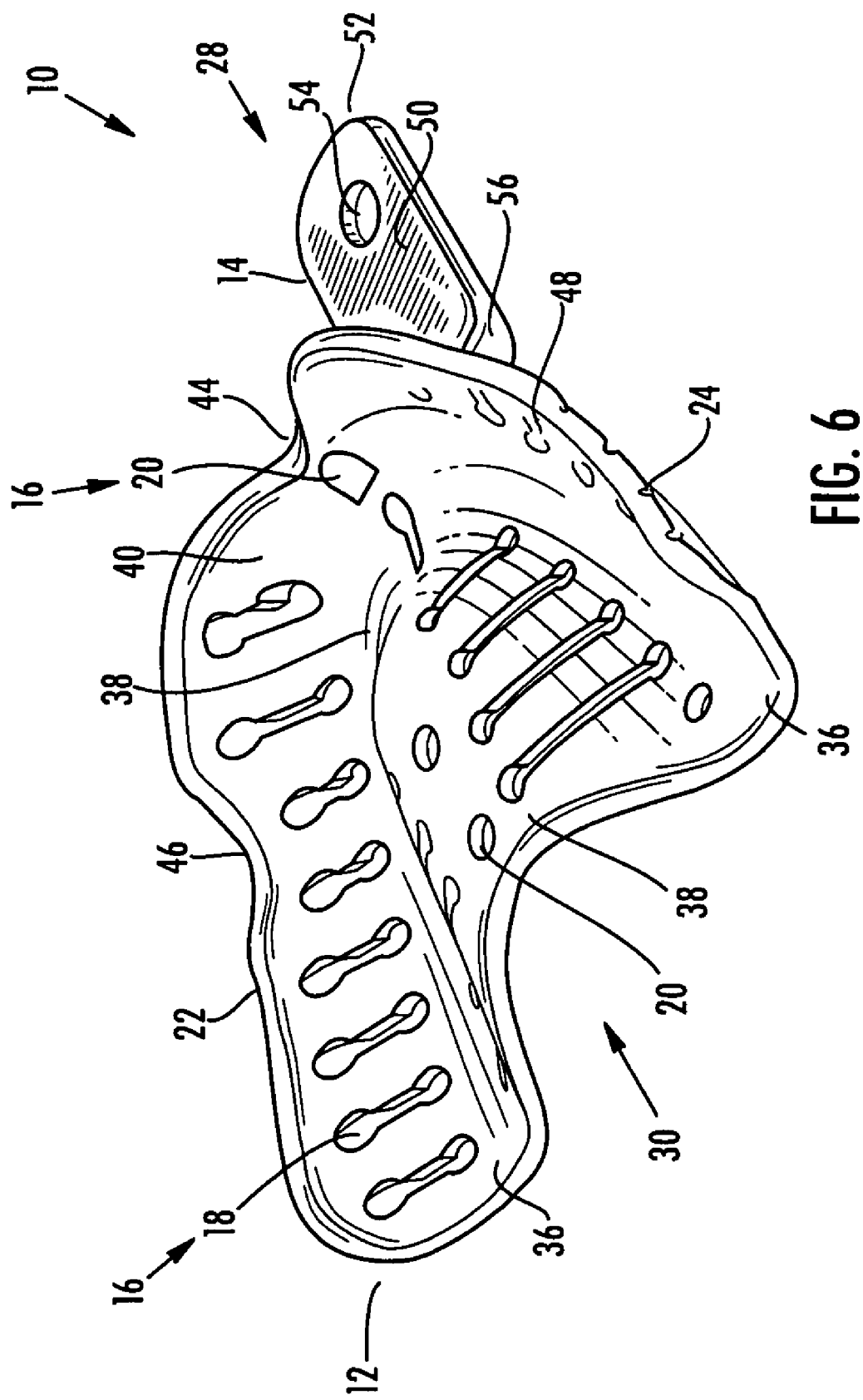
FIG. 6 is a top rear perspective view of the embodiment of the invention shown in FIG. 1.
Figure 7:
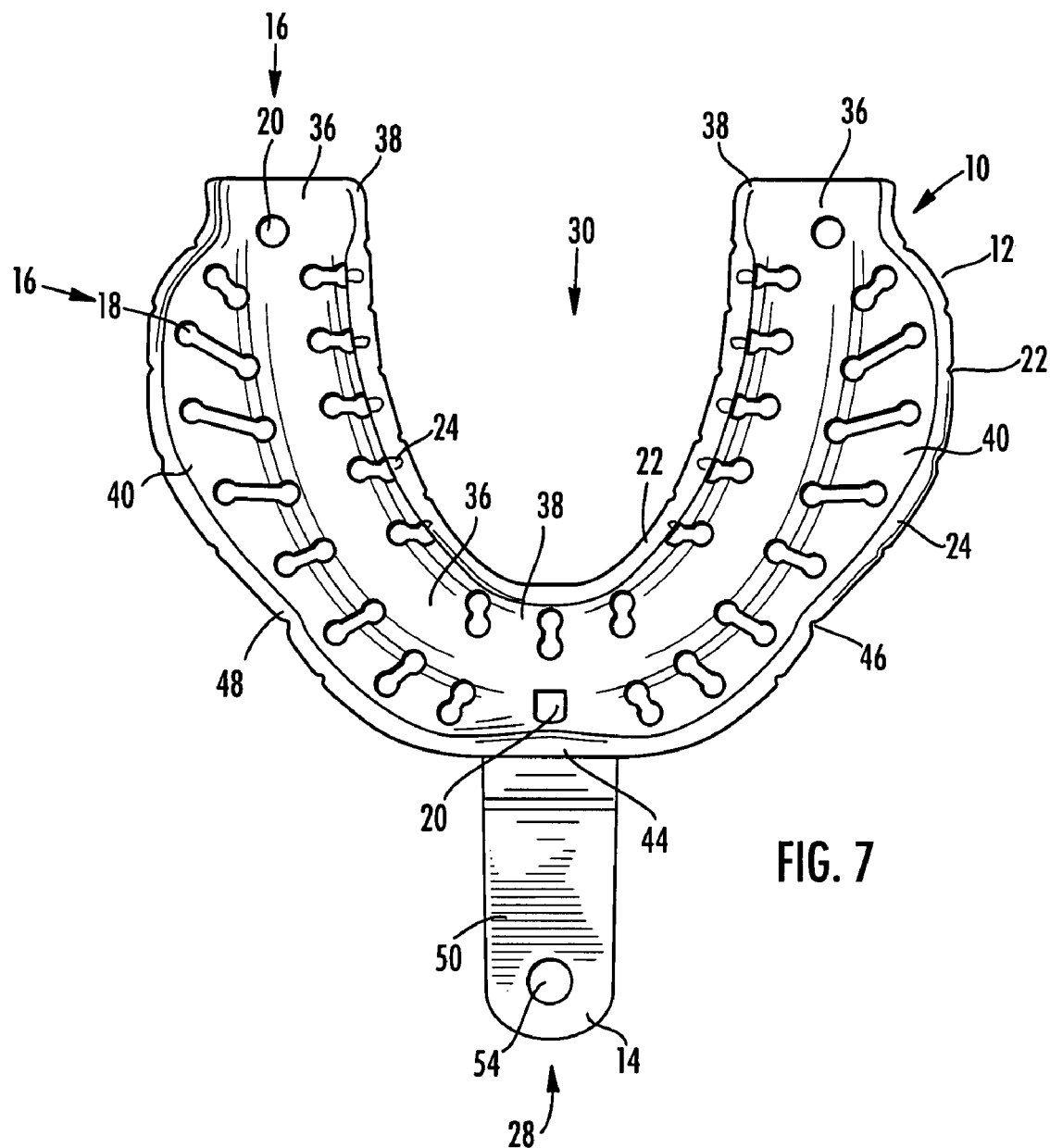
FIG. 7 is a top view of another embodiment of the invention.
Figure 8:
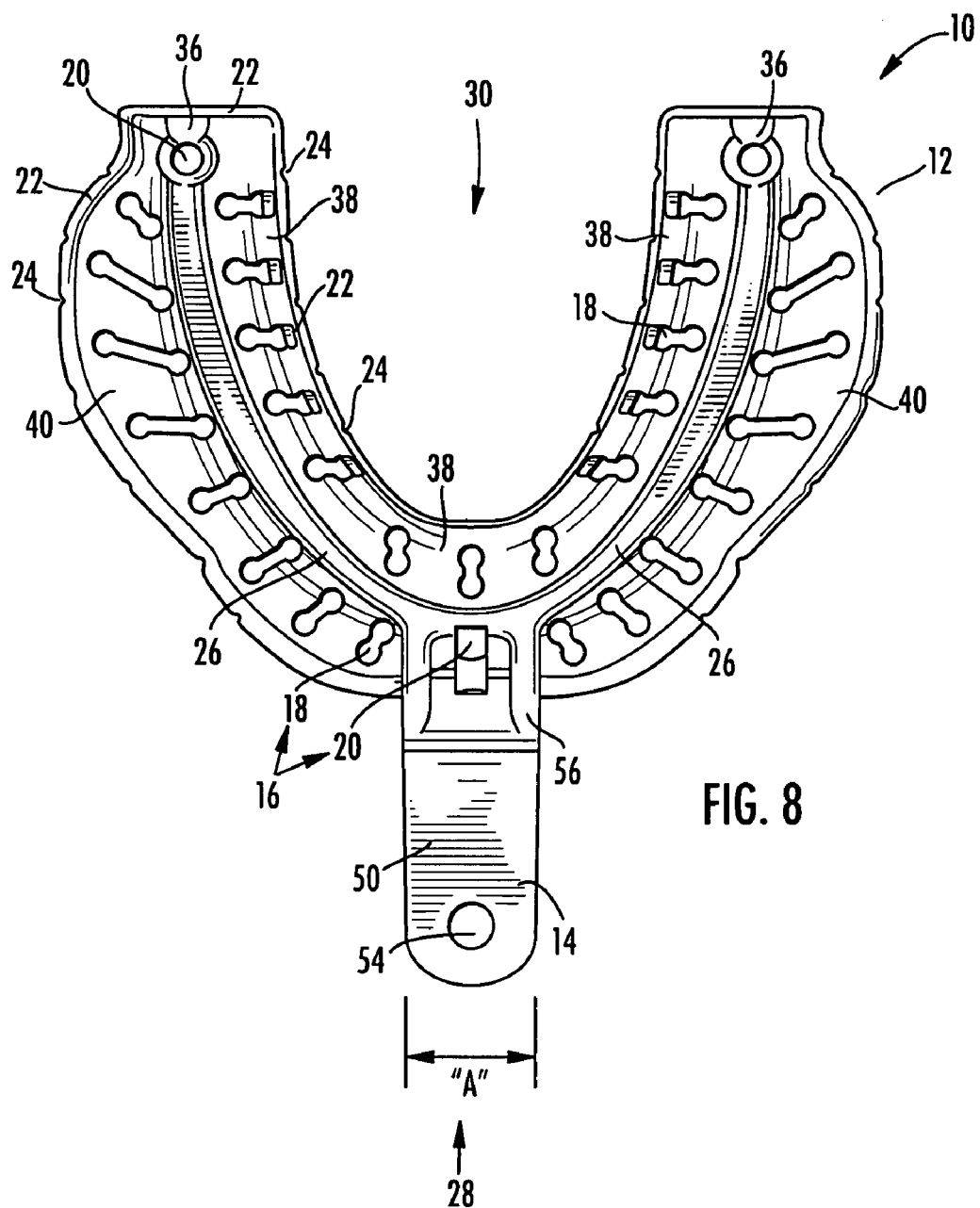
FIG. 8 is a bottom view of the embodiment of the invention shown in FIG. 7.
Figure 9:
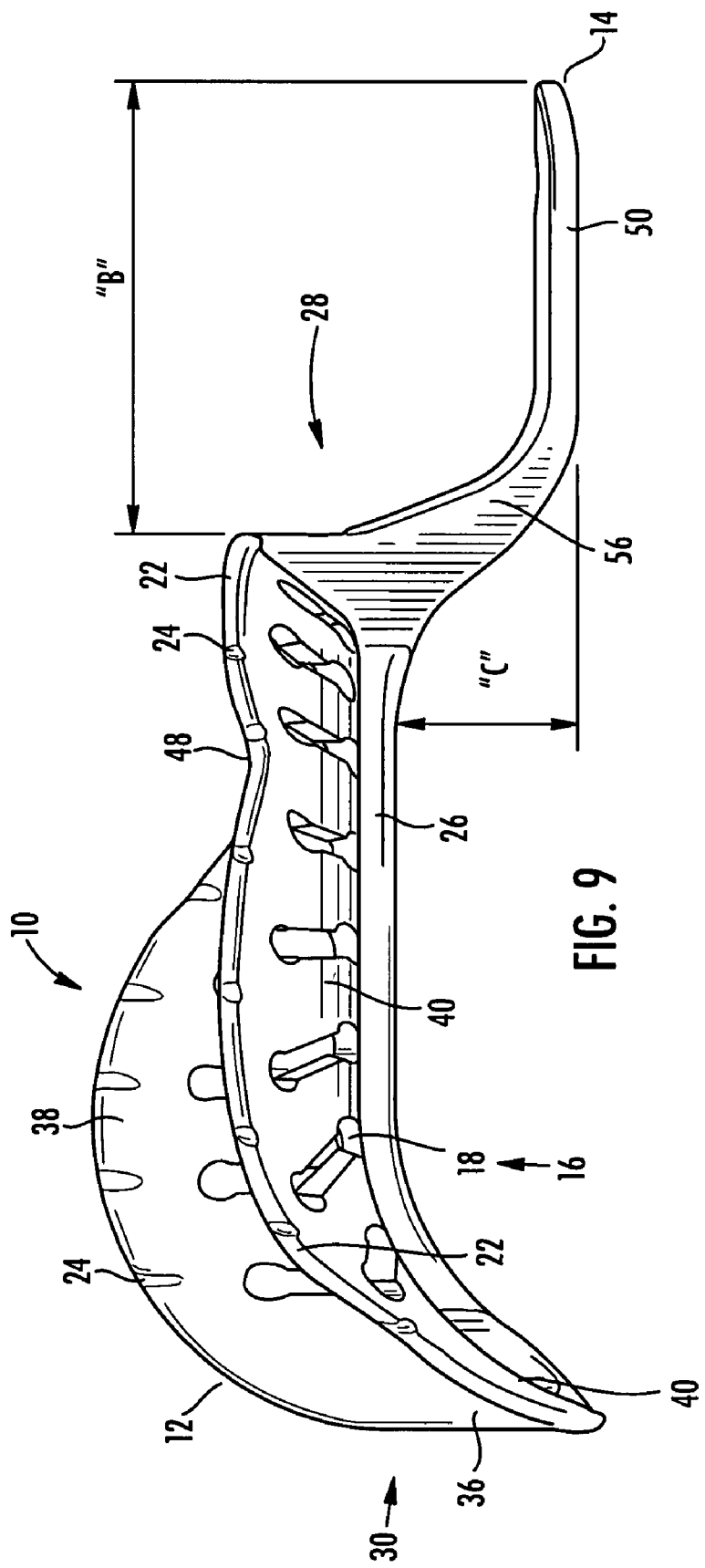
FIG. 9 is a side view of the embodiment of the invention shown in FIG. 7.
Figure 10:
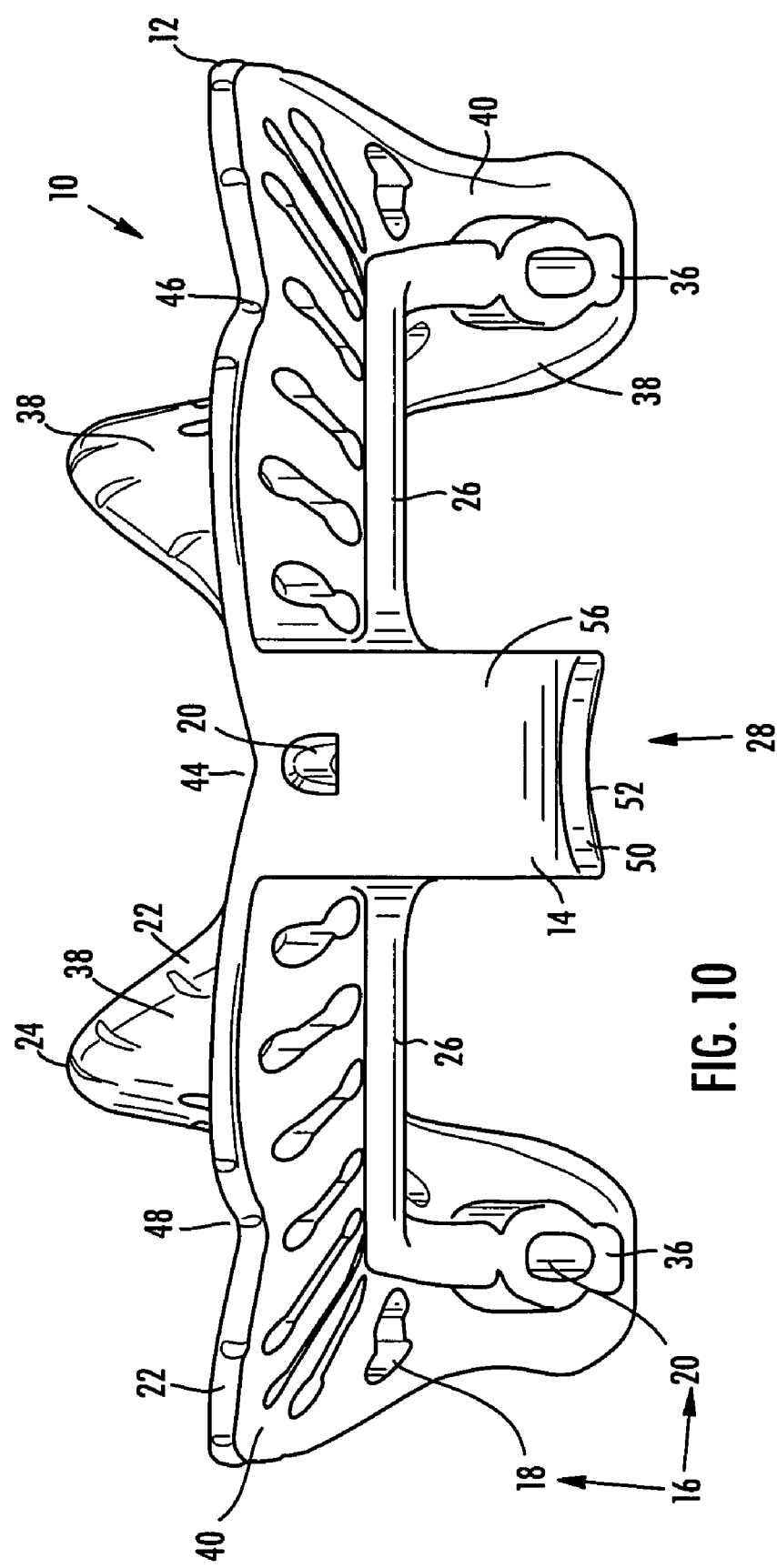
FIG. 10 is a front view of the embodiment of the invention shown in FIG. 7.
Figure 11:
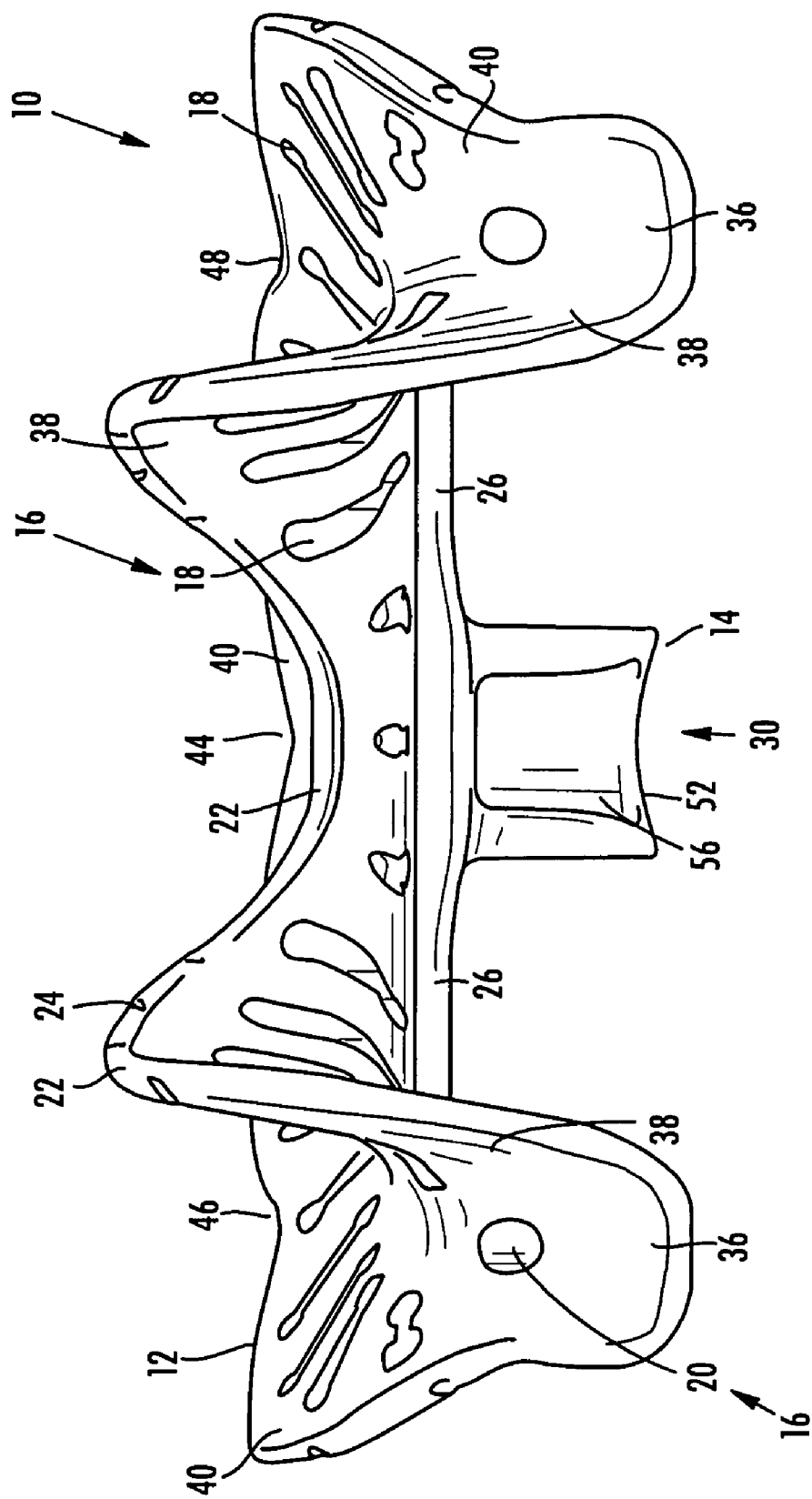
FIG. 11 is a rear view of the embodiment of the invention shown in FIG. 7.
Figure 12:
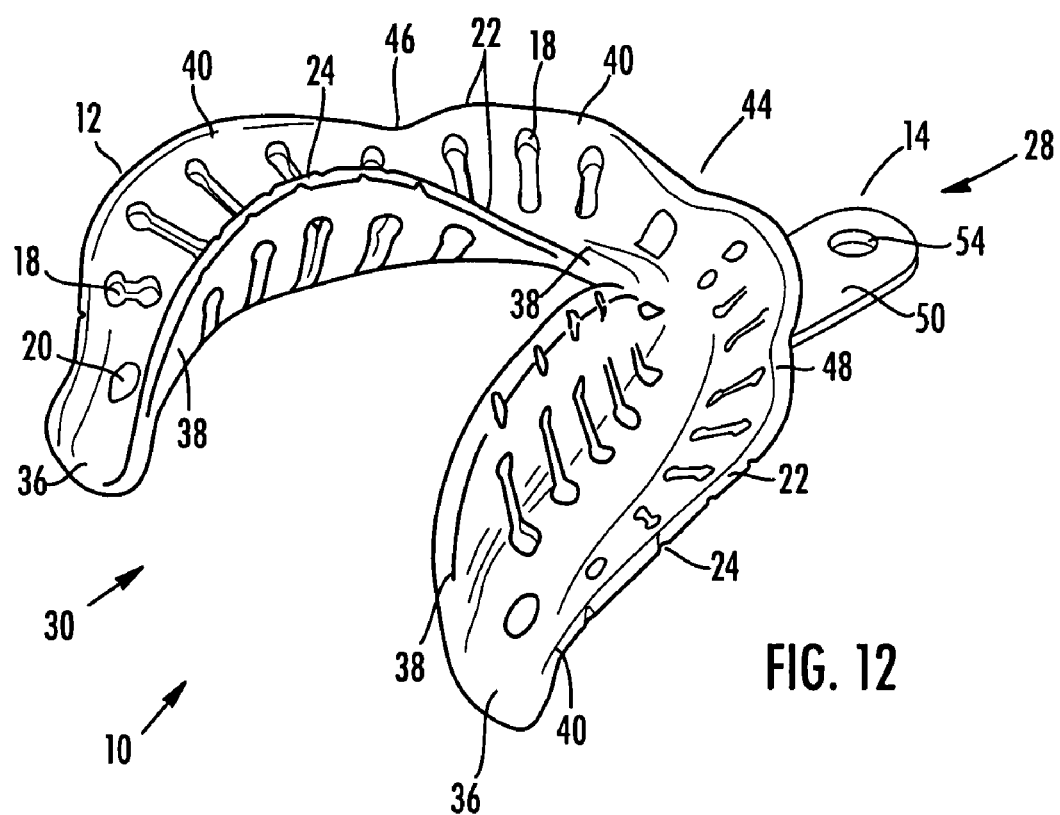
FIG. 12 is a top rear perspective view of the embodiment of the invention shown in FIG. 7.

As shown in FIGS. 2, 3, 8, & 9, the handle 14 is attached to the body 12 at the body front end 28. As shown on FIGS. 2 and 8, the handle 14 has a predetermined width dimension as indicated by the "A" dimension. As shown in FIGS. 3 and 9, the handle 14 has a predetermined length dimension as indicated by the "B" dimension and has a predetermined offset dimension as indicated by the "C" dimension, where the offset dimension is the distance between the bottom of body 12 and where the handle 14 is attached to the body 12, and the bottom of the handle 14.

The location and size of the handle in most prior art causes the handle to be a hindrance to obtaining an accurate impression as these handles: (1) force the operator to place their hand, wrist and arm in incorrect and uncomfortable positions while they place these dental trays and impression material into the mouth of the patient and while they are seating the dental impression tray and impression material in the patient's mouth during the process of obtaining the dental impression, which over time can injure the operator; (2) are so wide that the dental tray either traps or blocks the fingers of the operator when they attempt to seat the dental tray and impression material; (3) deforms the patient's lips which prevents the operator from obtaining an accurate impression and causes discomfort to the patient as it places pressure on the patient's lips; and (4) are not long enough to be used to by the operator to remove the dental tray and cured impression material which can lead to damaging or distorting the impression.

Ideally, the handle 14 width dimension needs to be narrow enough to fit between the fingers of the operator so that the operator can reach the bottom of the dental impression tray 10 to apply pressure to seat the dental impression tray 10 and impression materials, but wide enough to be used to insert and remove the dental impression tray 10 while it is retaining the impression material. The handle 14 length dimension needs to be long enough to extend past the patient's lips when taking the impression so that it can be effectively used to insert and remove the dental impression tray 10 and impression material, but short enough to not be in the way of the operator when the operator is seating the dental impression tray 10 and the impression materials. The handle 14 offset dimension needs to be long enough to allow the handle 14 to pass between the lips of the patient, but not so long that it is in the way of the operator or deform the patient's lips.

It has been determined that the desired dimension for the width or "A" dimension of the handle 14 is between 0.455 inches and 0.590 inches, the desired dimension for the length or "B" dimension of the handle 14 is between 0.970 inches and 1.398 inches, and the desired dimension for the offset or "C" dimension of the handle 14 is between 0.309 inches and 0.441 inches. These dimensions allow the handle 14 to be used to facilitate easy insertion and removal of the dental impression tray 10 and impression material from the patient's mouth; allows the handle 14 to be received between the fingers of the operator's hand comfortably to facilitate the operator being able to apply pressure to the bottom of each of the finger rest beams 26 to seat the dental impression tray 10 and impression material while keeping their hand, wrist and arm in an ergonomically correct position; and allows the handle 14 to line up with the patient's lips and extend past the patient's lips when taking the impression so that the handle 14 does not deform the patient's lips which allows for an accurate impression to be obtained and reduces the discomfort of the patient.

As shown in FIGS. 1 through 12, the handle 14 comprises a first handle section 50 and a second handle section 56. The first handle section 50 is connected to the upstanding outer wall portion 40 and the channel portion 36 of the body 12, at the body front end 28, by the second handle section 56 in the center of the body 12. The first handle section 50 being substantially a rectangular shaped sheet having a first handle section spherical shaped curvature 52 and a first handle opening 54, where the first handle section spherical shaped curvature 52 is in the horizontal plane when looking at the front of the body front end 28. The first handle section spherical shaped curvature 52 is designed for receiving the fat pads of the finger or thumb of the operator to significantly improve the operator's ability to grasp the first handle section 50 of the dental impression tray 10 during the impression process. The prior art provides handles that are straight or flat, which are more difficult to grasp during the impression process. The second handle section 56 having a predetermined shape and being received onto the upstanding outer wall portion 40 and the channel portion 36 of the body 12 to form the predetermined offset of the handle 14. The second handle section 56 also connects to each of the finger rest beams 26 that are received on the bottom of the channel portion 36 such that the first handle section 50, the second handle section 56 and each of the finger rest beams 26 cooperate to provide a mechanism to be used to engage the jaw and gingiva areas with the combination of the dental impression tray 10 and impression material or the combination of impression materials.

Whereas, the present invention has been described in relation to the drawings attached hereto, it should be understood that other and further modifications, apart from those shown or suggested herein, may be made within the spirit and scope of this invention.

What is claimed is:

1. A dental impression tray, used in cooperation with impression materials to obtain an impression of a jaw and gingiva areas of an edentulous patient, said dental impression tray comprising:

a. a body having a body front end, a body rear end, a predetermined shape of said body, and a plurality of body openings; said predetermined shape of said body accommodating the anatomical shape of the patient's mouth, said predetermined shape of said body being suitably dimensioned and configured to be placed around the entire jaw and gingiva areas while retaining the impression materials; said body openings positioned in said body at predetermined locations and having predetermined shapes such that the combination of said body openings locations and shapes cooperate with said body to allow the impression materials to vent through said body openings to obtain the impression of the jaw and gingiva areas of the patient and to retain the impression materials on said body, said body further comprising a thickened edge, substantially circular in shape with a predetermined diameter and being received along an outer edge of said body; said predetermined diameter being between 0.075 inches and 0.142 inches such that said thickened edge cooperates with said body and the impression materials to retain the impression materials on said body;

b. said thickened edge further comprising a plurality of edge notches positioned perpendicular to said thickened edge at predetermined locations on an exterior and an interior of said thickened edge such that said plurality of edge notches cooperate with said thickened edge and the impression materials to retain the impression materials on said body; and c. a handle having a predetermined width dimension, a predetermined length dimension, and a predetermined offset dimension, where the offset dimension is the distance between a bottom of said body and a bottom of said handle; said predetermined width dimension being between 0.455 inches and 0.590 inches, said predetermined length dimension being between 0.970 inches and 1.398 inches, and said predetermined offset dimension being between 0.309 inches and 0.441 inches; said handle comprising a first handle section, and a second handle section; said first handle section is connected to said body, at said body front end, by said second handle section, in the center of said body; said first handle section being substantially a rectangular shaped sheet having a first handle section spherical shaped curvature, where said first handle section spherical shaped curvature is in the horizontal plane when looking at the front of said body front end; and said second handle section having a predetermined shape where it is received onto said body to form said predetermined offset of said handle.

2. A dental impression tray as recited in claim 1, said dental impression tray further comprising at least two finger rest beams; each said finger rest beams having a predetermined shape and configuration to allow each said finger rest beams to be received longitudinally on the an exterior of said body such that each said finger rest beams are substantially located underneath the areas of said body that is to be placed around the jaw and gingiva areas of the patient; and each said finger rest beams are connected to said second handle section received on said body such that said handle and each said finger rest beams cooperate to provide a mechanism to be used to engage the jaw and gingiva areas with the combination of said dental impression tray and impression materials.

3. A dental impression tray as recited in claim 2, said plurality of body openings further comprising a plurality of substantially dumbbell shaped body openings and a plurality of substantially circular shaped body openings; said dumbbell shaped body openings having a variety of sizes and orientations, and said circular shaped body openings having a predetermined size, where said dumbbell shaped body openings and said circular shaped body openings are positioned in said body at predetermined locations such that the combination of the size, shape and location of said dumbbell shaped body openings and said circular shaped body openings cooperate with said body to allow the impression materials to vent through said dumbbell shaped body openings and said circular shaped body openings to obtain the impression of the jaw and gingiva areas of the patient and to retain the impression materials on said body.

4. A dental impression tray as recited in claim 1, said plurality of body openings further comprising a plurality of substantially dumbbell shaped body openings and a plurality of substantially circular shaped body openings; said dumbbell shaped body openings having a variety of sizes and orientations, and said circular shaped body openings having a predetermined size, where said dumbbell shaped body openings and said circular shaped body openings are positioned in said body at predetermined locations such that the combination of the size, shape and location of said dumbbell shaped body openings and said circular shaped body openings cooperate with said body to allow the impression materials to vent through said dumbbell shaped body openings and said circular shaped body openings to obtain the impression of the jaw and gingiva areas of the patient and to retain the impression materials on said body.

5. A dental impression tray, used in cooperation with impression materials to obtain an impression of a jaw and gingiva areas of an edentulous patient, said dental impression tray comprising:

a. a body having a body front end and a body rear end; said body comprising an upstanding outer wall portion, a channel portion and a central support portion; said upstanding outer wall portion having a first wall notch, a second wall notch and a third wall notch located along the top of said upstanding outer wall portion; said first wall notch, second wall notch and third wall notch being substantially V-shaped; said first wall notch being received in said upstanding outer wall portion at the center of said body front end, said second wall notch and third wall notch being received in the sides of upstanding outer wall portion approximately ⅓ of distance between said body front end and said body rear end such that said second wall notch and said third wall notch are closer to said body front end than to said body rear end; said central support portion having a substantially curved end at said body rear end; where the combination of said upstanding outer wall portion containing said first wall notch, said second wall notch and said third wall notch, said channel portion, and said central support portion containing said curved end at said body rear end having a predetermined shape and having a plurality of body openings; said predetermined shape accommodating the anatomical shape of a patient's mouth and being suitably dimensioned and configured to be placed around the entire jaw and gingiva areas while retaining the impression materials; said plurality of body openings comprising a plurality of substantially dumbbell shaped body openings and a plurality of substantially circular shaped body openings; said dumbbell shaped body openings having a variety of sizes and orientations, and said circular shaped body openings having a predetermined size, where said dumbbell shaped body openings and said circular shaped body openings are positioned in said body at predetermined locations such that the combination of the size, shape and location of said dumbbell shaped body openings and said circular shaped body openings cooperate with said body to allow the impression materials to vent through said dumbbell shaped body openings and said circular shaped body openings to obtain the impression of the jaw and gingiva areas of the patient, and to retain the impression materials on said body, where said upstanding outer wall portion being connected to said central support portion by said channel portion to form said body;

b. said body further comprising a thickened edge substantially circular in shape with a predetermined diameter and being received along the outer edge of said body; said predetermined diameter being between 0.075 inches and 0.142 inches such that said thickened edge cooperates with said body and the impression materials to retain the impression materials on said body;

c. said edge further comprising a plurality of edge notches positioned perpendicular to said thickened edge at predetermined locations on an exterior and an interior of said thickened edge such that said plurality of edge notches cooperate with said thickened edge and the impression materials to retain the impression materials on said body; and d. a handle having a predetermined width dimension, a predetermined length dimension, and a predetermined offset dimension, where the offset dimension is the distance between a bottom of said body and a the bottom of said handle; said predetermined width dimension being between 0.455 inches and 0.590 inches, said predetermined length dimension being between 0.970 inches and 1.398 inches, and said predetermined offset dimension being between 0.309 inches and 0.441 inches; said handle comprising a first handle section, and a second handle section; said first handle section is connected to said upstanding outer wall portions and said channel portion, at said body front end, by said second handle section, in the center of said body; said first handle section being substantially a rectangular shaped sheet having a first handle section spherical shaped curvature, where said first handle section spherical shaped curvature is in the horizontal plane when looking at the front of said body front end; and said second handle section having a predetermined shape where it is received onto said upstanding outer wall portion and said channel portion of said body to form said predetermined offset of said handle.

6. A dental impression tray as recited in claim 5, said dental impression tray further comprising at least two finger rest beams, each said finger rest beams having a predetermined shape and configuration to allow each said finger rest beams to be received longitudinally on an exterior of said channel portion of said body such that each said finger rest beams are substantially located underneath areas of said channel portion of said body that is to be placed around the jaw and gingiva areas of the patient; and each said finger rest beams are connected to said second handle section received on said channel portion of said body, such that said handle and each said finger rest beams cooperate to provide a mechanism to be used to engage the jaw and gingiva areas with the combination of said dental impression tray and impression materials.

7. A dental impression tray, used in cooperation with impression materials to obtain an impression of a jaw and gingiva areas of an edentulous patient, said dental impression tray being made from a heat moldable plastic material, said dental impression tray comprising:

a. a body having a body front end and a body rear end; said body comprising an upstanding outer wall portion, a channel portion, and a central support portion; said upstanding outer wall portion having a first wall notch, a second wall notch and a third wall notch located along the top edge of said upstanding outer wall portion; said first wall notch, second wall notch and third wall notch being substantially V-shaped; said first wall notch being received in said upstanding outer wall portion at the center of said body front end, said second wall notch and third wall notch being received in the sides of upstanding outer wall portion approximately ⅓ of distance between said body front end and said body rear end such that said second wall notch and said third wall notch are closer to said body front end than to said body rear end; said central support portion having a substantially curved end at said body rear end; where the combination of said upstanding outer wall portion containing said first wall notch, said second wall notch and said third wall notch, said channel portion, and said central support portion containing said curved end at said body rear end having a predetermined shape and having a plurality of body openings; said predetermined shape accommodating the anatomical shape of a patient's mouth and being suitably dimensioned and configured to be placed around the entire jaw and gingiva areas while retaining the impression materials; said plurality of body openings comprising a plurality of substantially dumbbell shaped body openings and a plurality of substantially circular shaped body opening; said dumbbell shaped body openings having a variety of sizes and orientations and said circular shaped body openings having a predetermined size, where said dumbbell shaped body openings and said circular shaped body openings are positioned in said body at predetermined locations, such that the combination of the size, shape and location of said dumbbell shaped body openings and said circular shaped body openings cooperate with said body to allow the impression materials to vent through said dumbbell shaped body openings and said circular shaped body openings to obtain the impression of the jaw and gingiva areas of the patient, and to retain the impression materials on said body, where said upstanding outer wall portion being connected to said central support portion by said channel portion to form said body; said body having a thickness between 0.072 inches and 0.094 inches to allow localized reshaping of said body by trimming of said body, where trimming is accomplished by an external cutter, or by heating and remolding of said body, where heating is accomplished with an external heating source, such that the reshaping of said body allows said predetermined shape of said body to be modified to specifically accommodate the patient'sjaw and gingiva areas which prevents deforming the gingiva areas of the patient's mouth when said dental impression tray is used in cooperation with impression materials to obtain an impression;

b. a handle having a predetermined width dimension, a predetermined length dimension, and a predetermined offset dimension, where the offset dimension is the distance between a bottom of said body and a bottom of said handle; said predetermined width dimension being between 0.455 inches and 0.590 inches, said predetermined length dimension being between 0.970 inches and 1.398 inches, and said predetermined offset dimension being between 0.309 inches and 0.441 inches; said handle comprising a first handle section, and a second handle section; said first handle section is connected to said upstanding outer wall portions and said channel portion, at said body front end, by said second handle section, in the center of said body, said first handle section being substantially a rectangular shaped sheet having a first handle section spherical shaped curvature, where said first handle section spherical shaped curvature is in the horizontal plane when looking at the front of said body front end; and said second handle section having a predetermined shape where it is received onto said upstanding outer wall portion and said channel portion of said body to form said predetermined offset of said handle; and c. at least two finger rest beams, each said finger rest beams being substantially a square shaped ridge received longitudinally on an exterior of said channel portion of said body such that each said finger rest beams are substantially located underneath areas of said channel portion that is to be placed around the jaw and gingiva areas of the patient; and each said finger rest beams are connected to said second handle section received on said channel portion, such that said handle and each said finger rest beams cooperate to provide a mechanism to be used to engage the jaw and gingiva areas with the combination of said dental impression tray and impression materials.

8. A dental impression tray as recited in claim 7, said body further comprising a thickened edge, said thickened edge being substantially circular in shape with a predetermined diameter and being received along an outer edge of said body; said predetermined diameter being between 0.075 inches and 0.142 inches such that said thickened edge cooperates with said body and the impression materials to retain the impression materials on said body.

9. A dental impression tray as recited in claim 8, said edge further comprising a plurality of edge notches, said plurality of edge notches being positioned perpendicular to said thickened edge at predetermined locations on an exterior and an interior of said thickened edge such that said plurality of edge notches cooperate with said thickened edge and the impression materials to retain the impression materials on said body.

10. A dental impression tray as recited in claim 9, said dental impression tray further comprising said moldable plastic material being a thermoplastic polymer material.

11. A dental impression tray as recited in claim 10, said dental impression tray further comprising said thermoplastic polymer material being polystyrene.

12. A dental impression tray as recited in claim 7, said dental impression tray further comprising said moldable plastic material being a thermoplastic polymer material.

\* \* \* \* \*